United States Patent [19]
O'Lenick, Jr.

[11] Patent Number: 6,013,813
[45] Date of Patent: Jan. 11, 2000

[54] GUERBET BASED SORBITAN ESTERS

[75] Inventor: Anthony J. O'Lenick, Jr., Dacula, Ga.

[73] Assignee: Hansotech Inc., Woodbury, N.Y.

[21] Appl. No.: 09/138,532

[22] Filed: Aug. 24, 1998

Related U.S. Application Data

[63] Continuation-in-part of application No. 09/098,790, Jun. 17, 1998.
[51] Int. Cl.⁷ .................................................. C07D 307/02
[52] U.S. Cl. .......................... 549/478; 549/429; 549/475; 549/476; 549/497; 549/499; 549/500; 554/227; 554/228; 554/229; 560/129

[58] Field of Search ..................................... 554/227, 228, 554/229; 560/124; 549/429, 475, 476, 478, 497, 499, 500

[56] References Cited

U.S. PATENT DOCUMENTS 2,322,821   6/1943   Brown et al. .

*Primary Examiner*—Deborah D Carr

[57] ABSTRACT

The present invention deals with the composition of matter and the utilization of certain novel sorbitol guerbet esters which are prepared by the reaction of a guerbet acid and a sorbitol as emulsifiers.

24 Claims, No Drawings

GUERBET BASED SORBITAN ESTERS

RELATED APPLICATIONS

This application is a continuation in part of Ser. No. 09/098,790, filed Jun. 17, 1998.

BACKGROUND OF THE INVENTION

1. Field of the Invention

The present invention deals with novel emulsifiers. The compounds are esters made by the reaction of sorbitol and guerbet acids. The introduction of the regiospecific branched guerbet acid portion of the molecule into the compounds of the present invention results in improved emulsification efficiency, improved oxidative stability and improved liquidity of the esters.

2. Description of the Art Practices

Guerbet alcohols have been known for many years. These materials can be oxidized into acids, which are raw materials for the preparation of the specific sorbitol esters of the present invention. They possess the critical regiospecific guerbet linkage which when placed into esters results in unexpected improvements in liquidity oxidative stability and emulsification properties of the resultant esters.

Sorbitan esters have likewise been known for years. U.S. Pat. No. 2,322,821 describes the chemistry.

THE INVENTION

This invention relates to the use of a particular group of regiospecific beta branched guerbet acids to prepare a esters. The esters are made by the reaction of a guerbet acid and a sorbitol to make a new series of unexpectedly efficient branched esters.

Esters are a class of compounds which find applications in many diverse segments of the chemical industry. One of the problems which is encountered using non-branched fatty acids to make sorbitol based esters is the fact that the resulting products are dark in color and possess a mal odor. It is very desirable, particularly in cosmetic applications to have products that are light in color and free of bad odors.

The specific structure of the esters of the present invention determines the functional attributes of the product, including odor, color, emulsification and liquidity. There are many possible structural variations which can impact upon the performance of esters. We have learned that the presence of a specific beta branching in the acid side of the molecule results in improved properties.

The compounds of the current invention are specific branched esters conforming to the following structure;

Sorbitan Mono Guerbet Esters

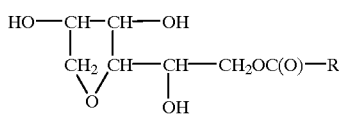

Wherein;
R is

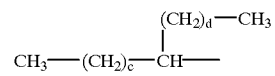

c and d are independently integers ranging from 3 to 14.

Sorbitan Di Guerbet Ester

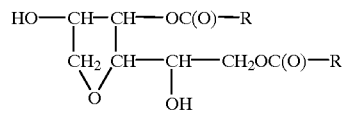

Wherein;
R is

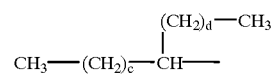

c and d are independently integers ranging from 3 to 14.

Sorbitan Tri-Guerbet Ester

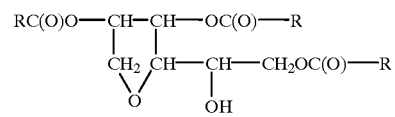

Wherein;
R is

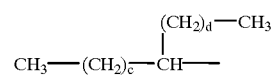

c and d are independently integers ranging from 3 to 14.

Preferred Embodiment

Sorbitan mono-guerbet Esters

In a preferred embodiment c and d are each 3.
In another preferred embodiment c and d are each 4.
In another preferred embodiment c and d are each 5.
In another preferred embodiment c and d are each 6.
In another preferred embodiment c and d are each 7.
In another preferred embodiment c and d are each 8.
In still another preferred embodiment c and d are each 14.

Sorbitan di-guerbet Esters

In a preferred embodiment c and d are each 3.
In another preferred embodiment c and d are each 4.
In another preferred embodiment c and d are each 5.
In another preferred embodiment c and d are each 6.
In another preferred embodiment c and d are each 7.
In another preferred embodiment c and d are each 8.
In still another preferred embodiment c and d are each 14.

3

Sorbitan tri-guerbet Esters

In a preferred embodiment c and d are each 3.

In another preferred embodiment c and d are each 4.

In another preferred embodiment c and d are each 5.

In another preferred embodiment c and d are each 6.

In another preferred embodiment c and d are each 7.

In another preferred embodiment c and d are each 8.

In still another preferred embodiment c and d are each 14.

EXAMPLES

Raw Materials

Guerbet Acids

Guerbet alcohols are oxidized into acids having the same regiospecific beta branched properties. This branching property present in the acid make products useful in the present invention.

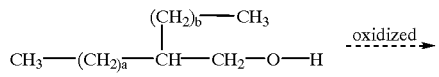

Guerbet Alcohol

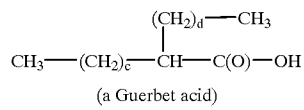

(a Guerbet acid)

Vista Chemical practices the oxidation of guerbet alcohols commercially. The values of c and d were actually determined by analysis and are not dependant upon trade name for meaning.

| Example | Commercial Name | c | d |
|---------|-----------------|-----|-----|
| 1 | Isocarb 10 | 3 | 3 |
| 2 | Isocarb 12 | 4 | 4 |
| 3 | Isocarb 14 | 5 | 5 |
| 4 | Isocarb 16 | 6 | 6 |
| 5 | Isocarb 18 | 7 | 7 |
| 6 | Isocarb 20 | 8 | 8 |
| 7 | Isocarb 32 | 14 | 14 |

Isocarb is a trademark of Vista.

Sorbitol

Sorbitol is a six carbon poly-hydroxy compound conforming to the following structure:

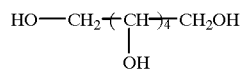

Sorbitol is an item of commerce and is generally sold as a 70% solution in water. The molecule undergoes a reaction under base conditions to cyclize. The optimum cyclization conditions are using KOH at a concentration of between 0.1 and 1.0%. Many ring containing compounds result. Details of the type of compounds produced are outlined in U.S. Pat. No. 2,322,821 incorporated herein by reference. The most simple and most common ring structure is:

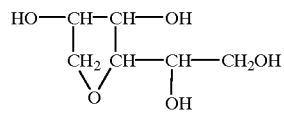

The compound above has four hydroxyl groups present that can be subsequently esterified by the guerbet acid. There are three classes of materials that we have made "Sorbitan Mono-Guerbet Esters" wherein one hydroxyl group is reacted, "Sorbitan Di-Guerbet Esters" wherein two hydroxyl groups are reacted, and "Sorbitan Tri-Guerbet Esters" wherein three hydroxyl groups are reacted. In a subsequent step, the remaining hydroxyl groups are ethoxylated to make a product that is more water soluble.

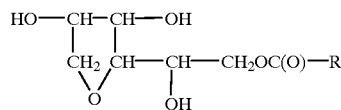

Sorbitan Mono-Guerbet Ester

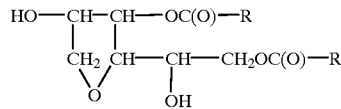

Sorbitan Di-Guerbet Ester

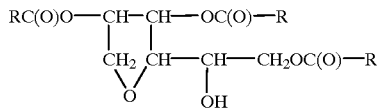

Sorbitan Tri-Guerbet Ester

Wherein;
R is

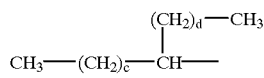

c and d are independently integers ranging from 3 to 14.

Sorbitol Cyclization 995.0 grams of 70% sorbitol in water is placed in a round bottom flask equipped with a condenser to remove water, vacuum and agitation. Nitrogen is applied to exclude air and keep the reaction product light in color. 10.0 grams of 45% KOH is then added. The reaction mass is heated to 100–105 C. to remove water. Once the water is removed, the temperature is increased to 180–200 C. and one mole of water is distilled off as the material cyclizes.

The resulting product is:

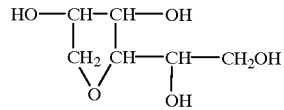

which is used without purification. We refer to this material as sorbitol intermediate. The structure is verified by hydroxyl value, and FTIR.

Ester Synthesis

The esterification reaction is typically carried out using one, two or three equivalents of guerbet acid. However, intermediate amounts can be used to make products that are mixtures. For example if 2.5 moles of acid are used, the resulting product will be a mixture of di and tri ester. The esterification reaction can be carried out with or without catalyst, however when no catalyst is used the reaction times are protracted. Catalysts like benzene sulfonic acid, tin, sulfuric acid, tin salts and the like can be used. The most satisfactory catalyst is stannous oxylate.

The ester is prepared by the esterification reaction as shown below:

$$HO-CH-CH-OH$$
$$\quad\quad\ |\quad\ |$$
$$CH_2\ CH-CH-CH-CH_2OH$$
$$\ \backslash O/\quad\quad\quad\ |$$
$$\quad\quad\quad\quad\quad OH$$

+

R—C(O)—OH   (Guerbet Acid)

heat ⋮ catalyst
↓

$$R-C(O)O-CH-CH-OC(O)R$$
$$\quad\quad\quad\quad\ |\quad\ |$$
$$CH_2\ CH-CH-CH-CH_2OC(O)-R$$
$$\ \backslash O/\quad\quad\quad\ |$$
$$\quad\quad\quad\quad\quad OH$$

wherein R is $$\quad\quad\quad\quad (CH_2)_d-CH_3$$
$$\quad\quad\quad\quad\ |$$
$$-CH_2-CH-(CH_2)_c-CH_3;$$

c and d are independently integers ranging from 3 to 14.

General Procedure

To the specified number of grams of guerbet acid (examples 1–7) is added 165.0 grams of sorbitol intermediate. Next add 0.1% stannous oxylate based upon the total weight of the batch after all ingredients have been charged, under agitation. The temperature of the mass is raised to 180–200 C. and water is stripped off as formed. The acid value and hydroxyl value drop to vanishingly small values, and the saponification value increases to theoretical.

The products are clear liquids and are liquid to extraordinary temperatures. They exhibit outstanding lubrication properties and are outstanding viscosity index modifiers.

Example 8

To 171.0 grams of guerbet acid (examples 1) is added to the sorbitol intermediate. Next add 0.1% stannous oxylate based upon the total weight of the batch after all ingredients have been charged, under agitation. The temperature of the mass is raised to 180–200 C. and water is stripped off as formed. The acid value and hydroxyl value drop to vanishingly small values, and the saponification value to increases to theoretical.

| Example | Guerbet Acid Example | Grams |
|---|---|---|
| Sorbitan Mono-Guerbet Esters | | |
| 9 | 1 | 175.0 |
| 10 | 2 | 199.0 |
| 11 | 3 | 227.0 |
| 12 | 4 | 255.0 |
| 13 | 5 | 283.0 |
| 14 | 6 | 311.0 |
| 15 | 7 | 479.0 |
| Sorbitan Di-Guerbet Esters | | |
| 16 | 7 | 958.0 |
| 17 | 6 | 622.0 |
| 18 | 5 | 566.0 |
| 19 | 4 | 510.0 |
| 20 | 3 | 454.0 |
| 21 | 2 | 398.0 |
| 22 | 1 | 513.0 |
| Sorbitan Tri-Guerbet Esters | | |
| 23 | 1 | 513.0 |
| 24 | 2 | 597.0 |
| 25 | 3 | 681.0 |
| 26 | 4 | 765.0 |
| 27 | 5 | 849.0 |
| 28 | 6 | 933.0 |
| 29 | 7 | 1439.0 |

The compounds of the present invention are liquid esters which are outstanding emulsifiers.

It is claimed:

1. A sorbitan mono-guerbet ester conforming to the following structure:

$$HO-CH-CH-OH$$
$$\quad\quad\ |\quad\ |$$
$$CH_2\ CH-CH-CH_2OC(O)-R$$
$$\ \backslash O/\quad\ |$$
$$\quad\quad\quad OH$$

Wherein
R is $$\quad\quad\quad\quad\quad (CH_2)_d-CH_3$$
$$\quad\quad\quad\quad\quad |$$
$$CH_3-(CH_2)_c-CH-$$

c and d are dependently integers ranging from 3 to 14.

2. A sorbitan mono-guerbet ester of claim 1 wherein c and d are each 3.

3. A sorbitan mono-guerbet ester of claim 1 wherein c and d are each 4.

4. A sorbitan mono-guerbet ester of claim 1 wherein c and d are each 5.

5. A sorbitan mono-guerbet ester of claim 1 wherein c and d are each 6.

6. A sorbitan mono-guerbet ester of claim 1 wherein c and d are each 7.

7. A sorbitan mono-guerbet ester of claim 1 wherein c and d are each 8.

8. A sorbitan mono-guerbet ester of claim 1 wherein c and d are each 14.

9. A sorbitan di-guerbet ester conforming to the following structure:

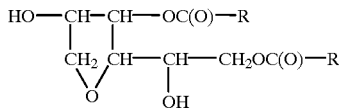

Wherein

R is

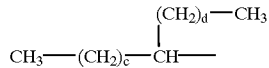

c and d are independently integers ranging from 3 to 14.

10. A sorbitan di-guerbet ester of claim 9 wherein c and d are each 3.

11. A sorbitan di-guerbet ester of claim 9 wherein c and d are each 4.

12. A sorbitan di-guerbet ester of claim 9 wherein c and d are each 5.

13. A sorbitan di-guerbet ester of claim 9 wherein c and d are each 6.

14. A sorbitan di-guerbet ester of claim 9 wherein c and d are each 7.

15. A sorbitan di-guerbet ester of claim 9 wherein c and d are each 8.

16. A sorbitan di-guerbet ester of claim 9 wherein c and d are each 14.

17. A sorbitan tri-guerbet ester conforming to the following structure:

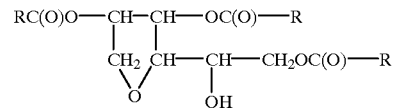

Wherein

R is

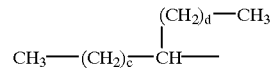

c and d are independently integers ranging from 3 to 14.

18. A sorbitan tri-guerbet ester of claim 17 wherein c and d are each 3.

19. A sorbitan tri-guerbet ester of claim 17 wherein c and d are each 4.

20. A sorbitan tri-guerbet ester of claim 17 wherein c and d are each 5.

21. A sorbitan tri-guerbet ester of claim 17 wherein c and d are each 6.

22. A sorbitan tri-guerbet ester of claim 17 wherein c and d are each 7.

23. A sorbitan tri-guerbet ester of claim 17 wherein c and d are each 8.

24. A sorbitan tri-guerbet ester of claim 17 wherein c and d are each 14.

* * * * *